(12) United States Patent
Dacus et al.

(10) Patent No.: US 10,619,238 B2
(45) Date of Patent: Apr. 14, 2020

(54) PROCESSES FOR PRODUCING ORTHOPEDIC IMPLANTS HAVING A SUBSURFACE LEVEL SILICON NITRIDE LAYER APPLIED VIA BOMBARDMENT

(71) Applicant: Joint Development, LLC, Salt Lake City, UT (US)

(72) Inventors: Eric M. Dacus, Salt Lake City, UT (US); Erin E. Hofmann, Park City, UT (US)

(73) Assignee: Joint Development, LLC, Salt Lake City, UT (US)

( * ) Notice: Subject to any disclaimer, the term of this patent is extended or adjusted under 35 U.S.C. 154(b) by 0 days.

(21) Appl. No.: 16/243,925

(22) Filed: Jan. 9, 2019

(65) Prior Publication Data

US 2019/0161856 A1    May 30, 2019

Related U.S. Application Data

(62) Division of application No. 15/670,534, filed on Aug. 7, 2017.

(Continued)

(51) Int. Cl.
| | |
|---|---|
| *C23C 16/24* | (2006.01) |
| *A61F 2/30* | (2006.01) |
| *A61L 27/34* | (2006.01) |
| *C23C 16/34* | (2006.01) |
| *C23C 16/48* | (2006.01) |

(52) U.S. Cl.
CPC ............ *C23C 16/24* (2013.01); *A61F 2/30* (2013.01); *A61L 27/34* (2013.01); *C23C 16/345* (2013.01); *C23C 16/486* (2013.01); *A61F 2002/30003* (2013.01); *A61F 2002/3006* (2013.01); *A61F 2002/30971* (2013.01); *A61F 2240/001* (2013.01); *A61F 2310/00874* (2013.01)

(58) Field of Classification Search
CPC combination set(s) only.
See application file for complete search history.

(56) References Cited

U.S. PATENT DOCUMENTS

| | | |
|---|---|---|
| 3,976,511 A | 8/1976 | Johnson |
| 4,790,851 A | 12/1988 | Suire et al. |
| | (Continued) | |

FOREIGN PATENT DOCUMENTS

| | | |
|---|---|---|
| GB | 2025238 | 1/1980 |

*Primary Examiner* — David H Willse
*Assistant Examiner* — Javier G Blanco
(74) *Attorney, Agent, or Firm* — Lowry Blixseth APC; Scott M. Lowry

(57) ABSTRACT

The process for producing an orthopedic implant having an integrated silicon nitride surface layer includes steps for positioning the orthopedic implant inside a vacuum chamber, mixing nitrogen gas and vaporized silicon atoms in the vacuum chamber, emitting a relatively high energy beam into the mixture of nitrogen gas and vaporized silicon atoms in the vacuum chamber to cause a gas-phase reaction between the nitrogen gas and the vaporized silicon atoms to form reacted precipitate silicon nitride molecules, and driving the precipitate silicon nitride molecules with the same beam into an outer surface of the orthopedic implant at a relatively high energy such that the precipitate silicon nitride molecules implant therein and form at least a part of the molecular structure of the outer surface of the orthopedic implant, thereby forming the integrated silicon nitride surface layer.

20 Claims, 6 Drawing Sheets

Related U.S. Application Data

(60) Provisional application No. 62/371,673, filed on Aug. 5, 2016.

(56) References Cited

U.S. PATENT DOCUMENTS

| | | |
|---|---|---|
| 5,520,664 A | 5/1996 | Bricault et al. |
| 6,361,567 B1 | 3/2002 | Dearnaley |
| 7,252,684 B2 | 8/2007 | Dearnaley |
| 7,704,546 B2 | 4/2010 | Dearnaley |
| 7,790,216 B2 | 9/2010 | Popoola et al. |
| 8,187,660 B2 | 5/2012 | Lawrynowicz et al. |
| 8,257,835 B2 | 9/2012 | Jani et al. |
| 2008/0255674 A1 | 10/2008 | Rahaman et al. |
| 2014/0277571 A1 | 9/2014 | Pettersson et al. |

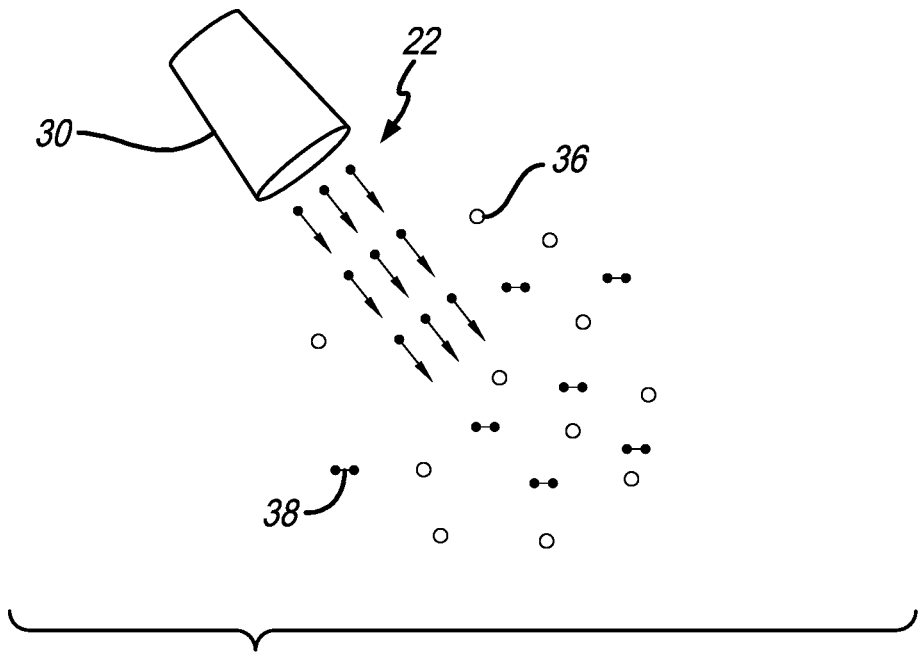
FIG. 3A
FIG. 3B
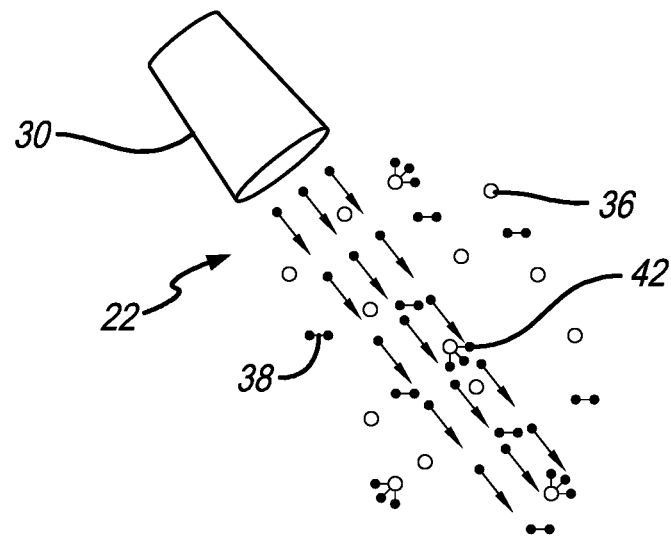

PROCESSES FOR PRODUCING ORTHOPEDIC IMPLANTS HAVING A SUBSURFACE LEVEL SILICON NITRIDE LAYER APPLIED VIA BOMBARDMENT

BACKGROUND OF THE INVENTION

The present invention generally relates to processes for producing orthopedic implants (e.g., hip, knee, shoulder replacements, etc.) having a subsurface level silicon nitride embedded layer applied via ion bombardment, and related implant products. More specifically, the present invention relates to using an ion beam to promote gas-phase reactions for subsequent relatively uniform layered implantation of reacted precipitate silicon nitride molecules into the subsurface of one or more target orthopedic implants.

Orthopedic implants (e.g., prosthetic joints to replace damaged hips, knees, shoulders, etc.) are commonly made of metal alloys such as cobalt chromium (CoCr) or titanium (Ti-6Al-4V). The mechanical properties of such metal alloys are particularly desirable for use in load-bearing applications, such as orthopedic implants. Although, when orthopedic implants are placed within the body, the physiological environment can cause the implant material to wear and corrode over time (especially articulatory surfaces), sometimes resulting in complications that require revision surgery. While hip and knee replacement surgery has been reported to be successful at reducing joint pain for 90-95% of patients, there are several complications that remain and the potential for revision surgery increases at a rate around 1% per year following a successful surgery. These complications can include infection and inflammatory tissue responses stemming from tribological debris particles from metal alloy implants, such as cobalt chromium, as a result of wear and corrosion over time.

To reduce the risk of complications from orthopedic implants, ceramic coatings have been applied to address the coefficient of friction of a wear couple, to specifically improve the surface roughness, and to reduce adhesion of a broad range of bacteria for purposes of reducing the rate of infection. For example, alumina ($Al_2O_3$) and zirconia ($ZrO_2$) are ceramics that have been used to coat the surfaces of orthopedic implants. These ceramic materials provide high wear resistance, reduced surface roughness, and high biocompatibility. But, both materials are not optimal for the fatigue loading of non-spherical geometry of most orthopedic implants due to poor tensile strength and low toughness. Accordingly, the disadvantages of these ceramic coatings, while addressing issues related to high wear resistance and surface roughness, cannot address other failure modes such as tensile strength and impact stresses.

Conventionally, ceramic coatings such as silicon nitride have been applied to the implant surface by a chemical vapor deposition (CVD) process or a physical vapor deposition (PVD) process. In one example, a PVD process is used to coat an implant joint with an external layer of silicon nitride. More specifically, such a process includes placing the implant, a silicon-containing material, and nitrogen gas ($N_2$) in a chamber that is heated to between 100-600 degrees Celsius. In response to the high temperatures, silicon atoms sputter from the silicon-containing material and subsequently react with the nitrogen gas at the heated surface of the implant to deposit a silicon nitride over-coat. One problem with this process is that there is no diffusion of the deposited silicon nitride molecules into the substrate material. That is, the silicon nitride is simply applied as an over-surface coating having a distinct boundary line between the deposited over-coating and the underlying substrate of the orthopedic implant. The adverse result is that the silicon nitride still experiences relatively poor surface adhesion and, over time, this over-surface coating can wear off, especially when the surface is an articulating surface (e.g., a ball-and-socket joint).

While vapor deposition of silicon nitride has been shown to work as an over-surface coating to certain orthopedic materials, such application is typically more expensive and less efficient than alumina or zirconia ceramic coatings. Moreover, it is often difficult, if not impossible, to attain a uniform application of silicon nitride to all surfaces of the orthopedic implant using known vapor deposition processes, such as those mentioned above. As a result, some areas of the over-surface coating have an undesirably thin layer of silicon nitride, wherein such areas are even more prone to reduced protection and wear. Alternatively, silicon nitride has also been used as the bulk or base material for orthopedic implants, but the production of a silicon nitride-based orthopedic implant is limited in size and inefficient to produce.

Recently, newer coating processes have been developed to provide greater adhesion by promoting diffusion of the coating material at the interface of the substrate and coating layers. Ion beam enhanced deposition (IBED), also known as ion beam assisted deposition (IBAD), is a process by which accelerated ions drive a vapor phase coating material into the subsurface of a substrate. Coatings applied by IBED may have greater adhesion than similar coatings applied by a conventional PVD process. Coatings applied by IBED may also have less delamination under impact stresses. For example, U.S. Pat. No. 7,790,216 to Popoola et al., the contents of which are herein incorporated by reference in their entirety, discloses a method of bombarding a medical implant with zirconium ions and then heating the implant in an oxygenated environment to induce the formation of zirconia ($ZrO_2$) at the surface. In this respect, the ion beam drives the zirconium ions to a certain depth within the surface of the implant known as the "intermix zone". Heat treatment within the oxygenated environment results in an embedded zirconia surface layer of approximately 5 micrometer ($\mu$m) thickness. The zirconia surface layer effectively penetrates the substrate and thereby resists delamination. But, this production method can be inefficient due to the high energy requirement for the heat treatment step. Likewise, the mechanical properties of the zirconia surface layer formed are not as desirable as those of a silicon nitride surface layer, which is incompatible with a heat treatment step.

There exists, therefore, a need in the art for processes for producing orthopedic implants having a subsurface silicon nitride layer applied via ion bombardment that provides greater integration of silicon nitride into the implant, thereby providing greater resistance to the emission of tribological debris. Such processes may include placing an orthopedic implant in a vacuum chamber, diffusing gaseous nitrogen and silicon within the chamber, and bombarding a surface of the orthopedic implant with an ion beam sufficient to promote gas-phase reactions to form silicon nitride and drive reacted precipitate silicon nitride molecules into the subsurface of the medical implant. The present invention fulfills these needs and provides further related advantages.

SUMMARY OF THE INVENTION

In one embodiment, a process for producing an orthopedic implant having an integrated silicon nitride surface layer as disclosed herein may include steps for positioning the orthopedic implant inside a vacuum chamber, mixing nitrogen gas and vaporized silicon atoms in the vacuum chamber, emitting a relatively high energy beam into the mixture of nitrogen gas and vaporized silicon atoms in the vacuum chamber to cause a gas-phase reaction between the nitrogen gas and the vaporized silicon atoms to form reacted precipitate silicon nitride molecules, and driving the precipitate silicon nitride molecules with the same beam into an outer surface of the orthopedic implant at a relatively high energy such that the precipitate silicon nitride molecules implant therein and form at least a part of the molecular structure of the outer surface of the orthopedic implant, thereby forming the integrated silicon nitride surface layer. An intermix layer may be formed underneath the integrated silicon nitride surface layer, depending on the energy intensity of the beam. Here, the intermix layer may include a mixture of the precipitate silicon nitride molecules and a base material of the orthopedic implant.

In one aspect of this embodiment, the beam may include an ion beam that emits nitrogen ions selected from the group consisting of N+ ions or N2+ ions. Accordingly, the emitting step may include delivering the nitrogen ions at a rate of about 1-5 nitrogen ions for each vaporized silicon atom. In this embodiment, when the rate is about one nitrogen ion for each silicon atom, the integrated silicon nitride surface layer may include $Si_3N_4$. Alternatively, when the rate is about five nitrogen ions for each silicon atom, the integrated silicon nitride surface layer may include $SiN_3$. During the driving step, the beam may also include an energy level greater than 102 kiloelectron volts (KeV), yet the temperature of the outer surface of the orthopedic implant may be below 200 degrees Celsius. The beam may propagate relative to the orthopedic implant, or the positioning step may include mounting the orthopedic implant to a selectively movable platen for repositioning an orientation of the orthopedic implant relative to the beam.

In other aspects of this embodiment, the outer surface of the orthopedic implant may be cleaned prior to or during implantation by setting the beam to an energy level between about 1-1000 electron volts. Additionally, an evaporator positioned within the vacuum chamber may vaporize silicon atoms off a silicon ingot at a rate determined by the desired ratio of nitrogen molecules to silicon atoms inside the vacuum chamber at any given time during the process. Here, for example, the formation rate of the precipitate silicon nitride molecules may be regulated by adjusting the beam energy or beam density. Additionally, the quantity of nitrogen gas and/or the quantity of vaporized silicon atoms may be further controlled by backfilling the vacuum chamber with the same. The resultant integrated silicon nitride surface layer may have a substantially uniform thickness where the silicon nitride molecules are driven into the orthopedic implant. In some embodiments, the driving step may include the step of applying the integrated silicon nitride surface layer to less than an entire outer surface area of the orthopedic implant. The integrated silicon nitride surface layer may substantially include the silicon nitride molecules.

In another process disclosed herein, producing an orthopedic implant having an integrated silicon nitride surface layer may include steps for positioning the orthopedic implant inside a vacuum chamber, vaporizing silicon atoms off a silicon ingot with an evaporator, mixing nitrogen gas and the vaporized silicon atoms in the vacuum chamber, and emitting a relatively high energy beam having an energy level greater than 102 kiloelectron volts (KeV) into the mixture of nitrogen gas and vaporized silicon atoms in the vacuum chamber to cause a gas-phase reaction between the nitrogen gas and the vaporized silicon atoms, thereby forming reacted precipitate silicon nitride molecules. The outer surface of the orthopedic implant may be cleaned with the beam by setting the initial energy level between about 1-1000 electron volts. Thereafter, the precipitate silicon nitride molecules may be driven with the same beam into the outer surface of the orthopedic implant albeit at the same or a relatively higher energy level such that the precipitate silicon nitride molecules implant therein and form at least a part of the molecular structure of the outer surface of the orthopedic implant simultaneously while maintaining the outer surface of the orthopedic implant at a temperature below 200 degrees Celsius. Such a process may form the integrated silicon nitride surface layer therein.

The orthopedic implant may be mounted to a selectively movable platen within the vacuum chamber for repositioning an orientation of the orthopedic implant relative to the beam. In this embodiment, the formation rate of the precipitate silicon nitride molecules may be regulated by adjusting the beam energy or beam density. The driving step may also include the step of applying the integrated silicon nitride surface layer to less than an entire outer surface area of the orthopedic implant. Additionally, backfilling the vacuum chamber with the nitrogen gas or the vaporized silicon atoms may maintain the desired ratios, i.e., in an embodiment where the beam includes an ion beam including nitrogen ions selected from the group consisting of N+ ions or N2+ ions, the emitting step may include the step of delivering the nitrogen ions at a rate of about 1-5 nitrogen ions for each vaporized silicon atom. When the rate is about one nitrogen ion for each silicon atom, the integrated silicon nitride surface layer may include $Si_3N_4$, and, when the rate is about five nitrogen ions for each silicon atom, the integrated silicon nitride surface layer may include $SiN_3$.

In another aspect of this embodiment, an intermix layer may be formed underneath the integrated silicon nitride surface layer. Here, the intermix layer may include a mixture of the precipitate silicon nitride molecules and a base material of the orthopedic implant. The integrated silicon nitride surface layer may include a substantially uniform thickness where driven into the orthopedic implant, such as by a propagating the beam, and the integrated silicon nitride surface layer may substantially include the silicon nitride molecules.

In another embodiment, an orthopedic implant as disclosed herein may include or be made from a base material that includes a metal alloy selected from the group consisting of cobalt, titanium, and zirconium, a ceramic material selected from the group consisting of alumina ($Al_2O_3$) and zirconia ($ZrO_2$), an organic polymer, or a composite organic polymer. The orthopedic implant may also include an intermix layer that includes a mixture of the base material and a plurality of silicon-based molecules (e.g., $Si_3N_4$ or $SiN_3$) implanted into the base material. The intermix layer may include a thickness of about 0.1-100 nanometers and include a subsurface level of silicon-based molecules.

Additionally, the orthopedic implant may include an integrated silicon nitride surface layer forming at least part of a molecular structure of an outer surface of the orthopedic implant. Here, the integrated silicon nitride surface layer and the base material may cooperate with one another to sandwich the intermix layer in between. In one embodiment, the integrated silicon nitride surface layer may have a relatively uniform depth. In another embodiment, the integrated silicon nitride surface layer may cover less than an entire surface area of the base material. The base material may include the integrated silicon nitride surface layer on an articulating surface only and the orthopedic implant may have an electrical resistivity of about 1016 Ω·cm when incorporating the integrated silicon nitride surface layer therein.

In other aspects of the embodiments disclosed herein, the silicon nitride surface layer and the base material may form an alloy bond therebetween at an atomic level by ion bombardment. The intermix layer and the integrated silicon nitride surface layer may have an aggregate thickness of about 1-10,000 nanometers and the orthopedic implant may include a hip implant, a knee implant, or a shoulder implant.

In another embodiment of an orthopedic implant as disclosed herein, the orthopedic implant may generally be made from a base material that includes a metal alloy selected from the group consisting of cobalt, titanium, and zirconium, a ceramic material selected from the group consisting of alumina ($Al_2O_3$) and zirconia ($ZrO_2$), an organic polymer, or a composite organic polymer. An intermix layer having a thickness of about 0.1-100 nanometers may include a mixture of the base material and a plurality of subsurface level silicon-based molecules implanted into the base material. The silicon-based molecules may include $Si_3N_4$ or $SiN_3$, and the integrated silicon nitride surface layer may cover less than an entire surface area of the base material. Additionally, the orthopedic implant may include an integrated silicon nitride surface layer having a relatively uniform thickness and forming at least part of the molecular structure of an articulating surface of the orthopedic implant. Here, the integrated silicon nitride surface layer and the base material may cooperate to sandwich the intermix layer in between. The intermix layer and the integrated silicon nitride surface layer may have an aggregate thickness of about 1-10,000 nanometer and the orthopedic implant incorporating the integrated silicon nitride surface layer may have an electrical resistivity of about 1016 Ω·cm.

In another aspect, the processes disclosed herein for producing orthopedic implants having a subsurface level silicon nitride layer implanted via ion bombardment may include mounting an orthopedic implant to an angling and/or rotating part platen assembly located inside a vacuum chamber. An ion beam generator may emit a beam of energized ions that bombard an outer surface of the angling and/or rotating orthopedic implant to cleanse the surface of contaminants. The chamber may then be filled with a gaseous mixture of vaporized silicon atoms and nitrogen gas molecules. The ion beam excites the gaseous silicon atoms and nitrogen molecules to promote a reaction that forms silicon nitride. The ion beam subsequently drives the precipitated silicon nitride molecules into the angling and/or rotating surface of the orthopedic implant to form an ion bombarded subsurface layer of silicon nitride, the depth of which depends on the intensity of the ion beam driving the silicon nitride molecules into the subsurface of the orthopedic implant.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 3a is a diagrammatic view illustrating interaction of an ion beam with a gaseous mixture of vaporized silicon atoms and nitrogen gas molecules;

FIG. 3b is a diagrammatic view illustrating the ion beam promoting reaction of the gaseous mixture of the vaporized silicon atoms and the nitrogen gas molecules to form gaseous silicon nitride molecules;

DETAILED DESCRIPTION OF THE PREFERRED EMBODIMENTS

Figure 1:
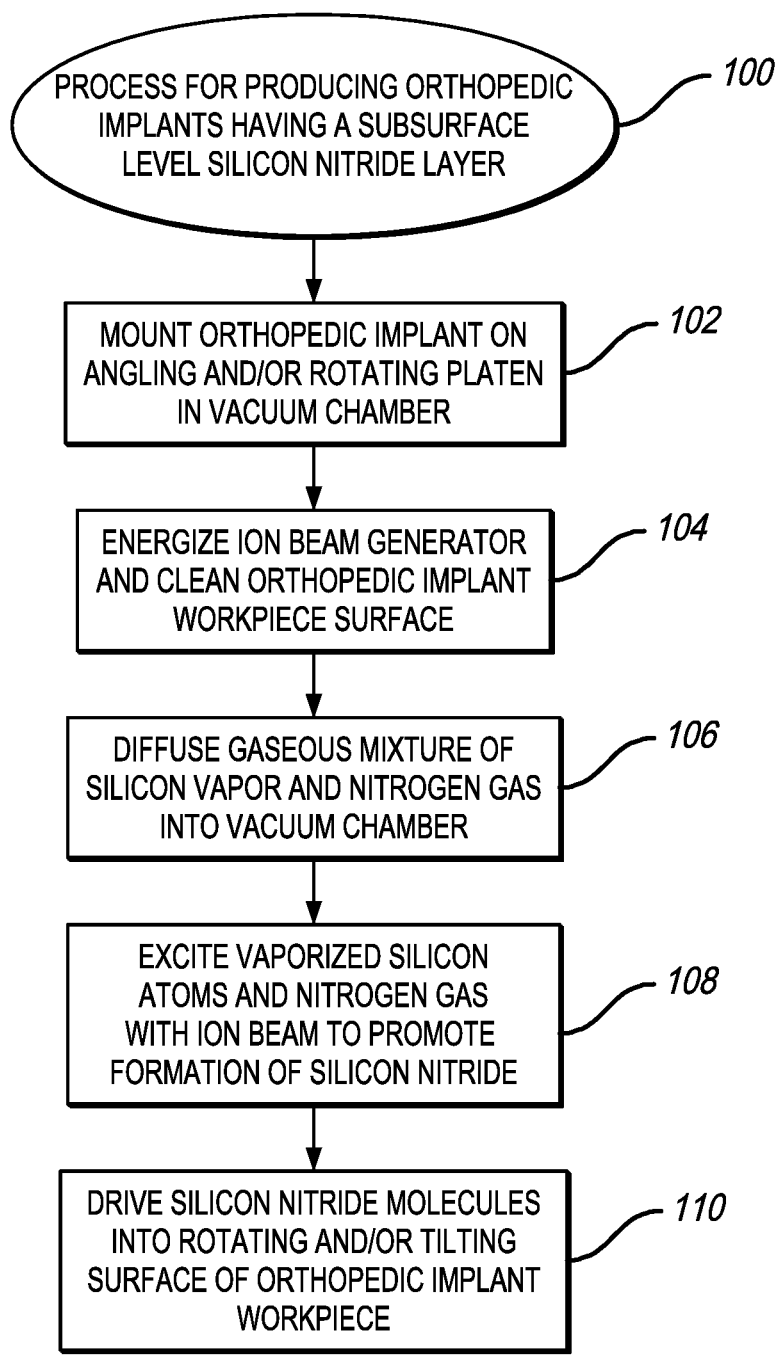
FIG. 1 is a flowchart illustrating a process for producing orthopedic implants having a subsurface level silicon nitride bombardment layer, as disclosed herein.
Figure 4A:
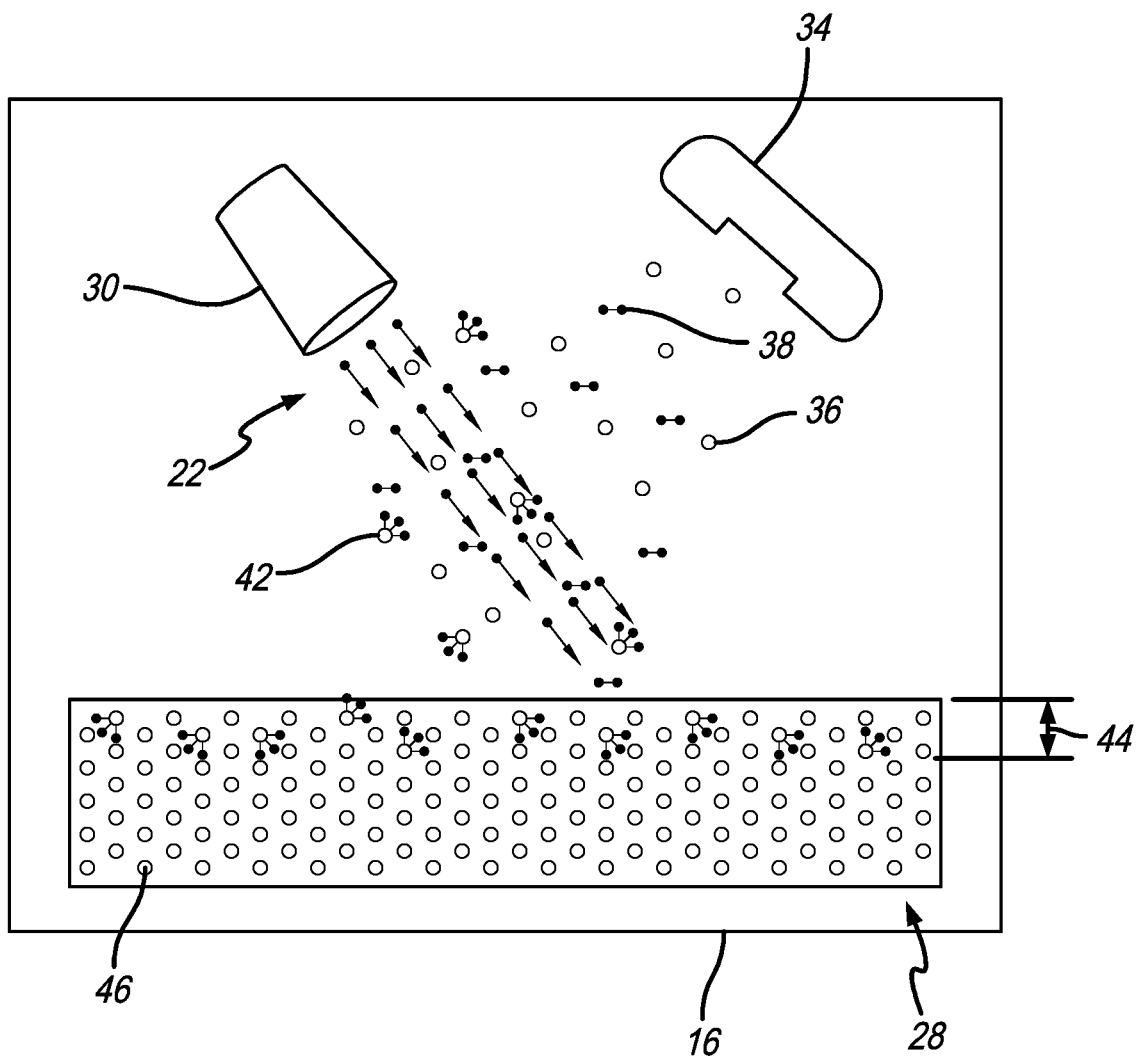
FIG. 4a is a diagrammatic view illustrating the ion beam driving the gaseous silicon nitride molecules into the angling and/or rotating surface of the orthopedic implant, thereby forming a subsurface intermixed layer.
Figure 4B:
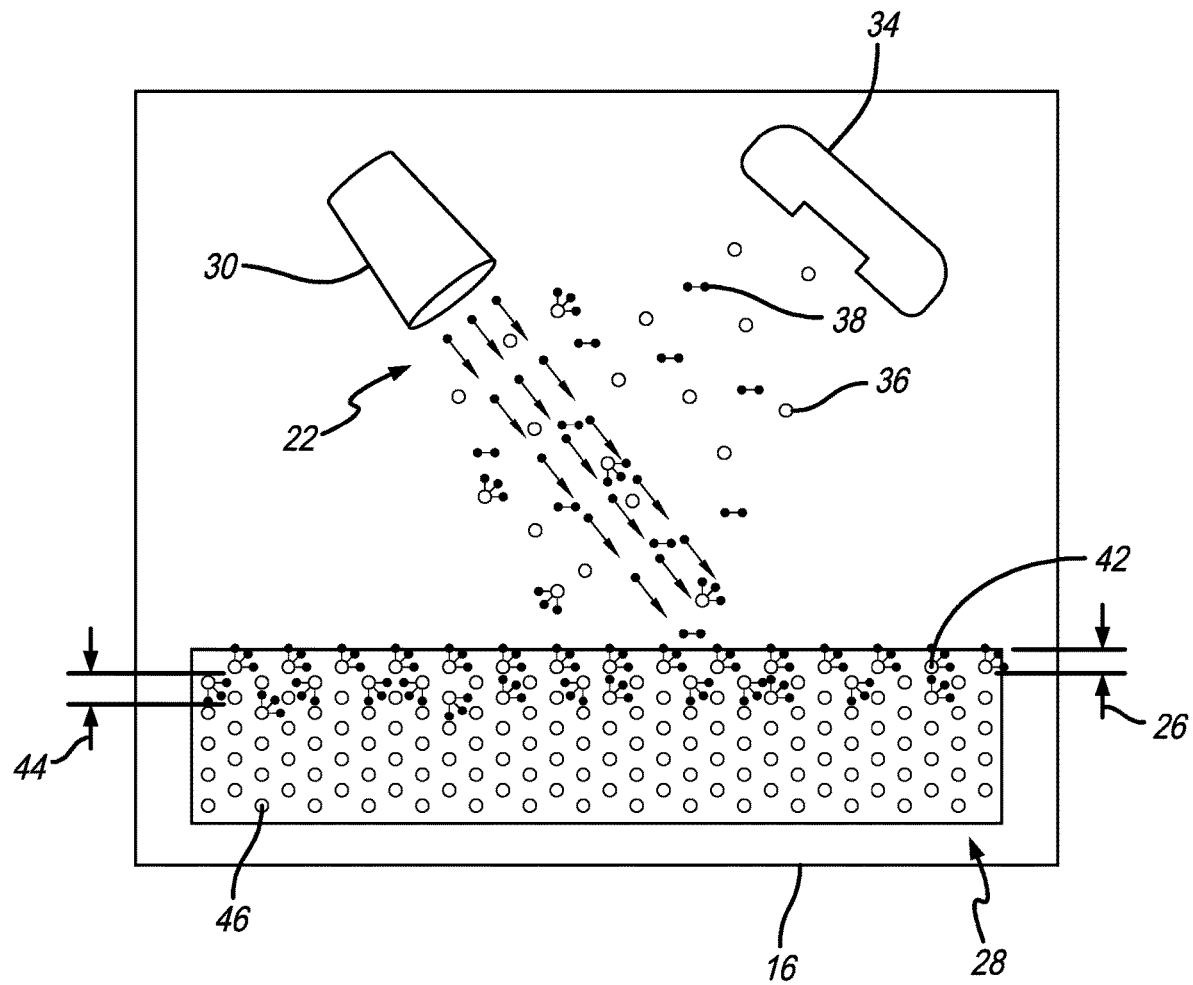
FIG. 4b is a diagrammatic view illustrating the ion beam further driving the gaseous silicon nitride molecules into the angling and/or rotating surface of the orthopedic implant, thereby forming a subsurface silicon nitride layer of relatively uniform thickness over the subsurface intermixed layer.
Figure 5:
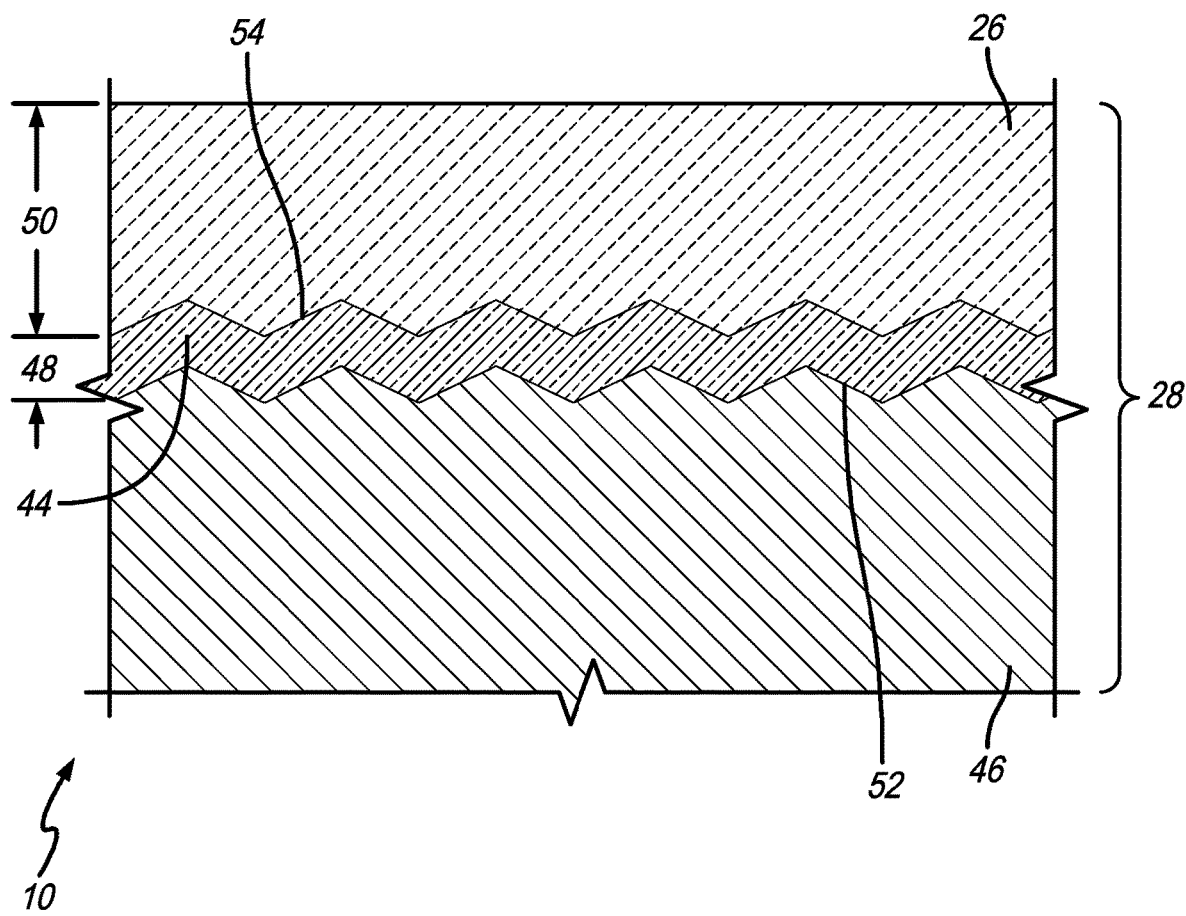
FIG. 5 is a cross-sectional view of the orthopedic implant having the subsurface silicon nitride layer produced by the ion beam implantation or bombardment of the gaseous silicon nitride molecules therein.

As shown in the exemplary drawings for purposes of illustration, the processes for producing orthopedic implants having a subsurface level silicon nitride bombardment layer is referred to by numeral (100) with respect to the flowchart in FIG. 1, while FIGS. 2-4b more specifically illustrate the operation of said processes, and FIG. 5 illustrates an exemplary orthopedic implant with a subsurface level silicon nitride bombardment layer 10. More specifically, the first step (102) in the process (100), as shown in FIG. 1, is to mount an orthopedic implant workpiece 12 onto an angling and/or rotating part platen 14 inside a vacuum chamber 16 suitable for performing ion beam implantation (e.g., ion beam enhanced deposition (IBED)). The processes disclosed herein improve the integration of silicon nitride into the orthopedic implant by kinetically driving silicon nitride molecules into a subsurface layer of the orthopedic implant. This improved integration of silicon nitride reduces delamination and prevents future wear and corrosion. Furthermore, the processes disclosed herein can reduce energy costs by performing the IBED process at temperatures well below 200 degrees Celsius and without a heat treatment step. Accordingly, the processes disclosed herein also reduce energy costs associated with manufacturing the related implant products.

Figure 2:
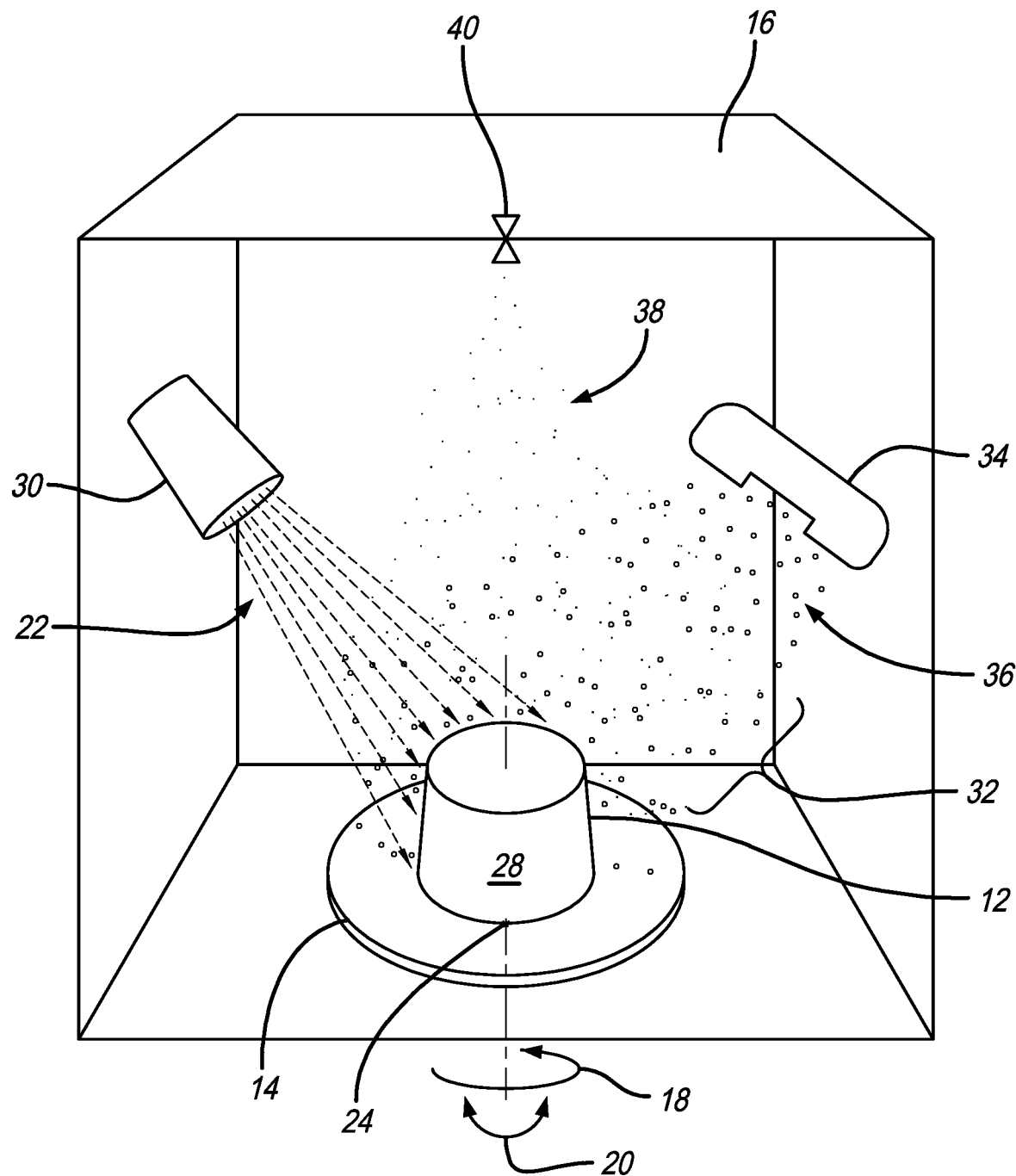
FIG. 2 is a diagrammatic view of an ion beam enhanced deposition (IBED) chamber, in accordance with the embodiments disclosed herein.

More specifically, FIG. 2 illustrates the orthopedic implant workpiece 12 mounted to the angling and/or rotating part platen 14 within the vacuum chamber 16. The orthopedic implant workpiece 10 may be made from a variety of metal alloys known in the art, such as cobalt, titanium, zirconium alloy, etc. In other embodiments, the orthopedic implant workpiece 10 may be made from ceramic materials known in the art, such as alumina ($Al_2O_3$) or zirconia ($ZrO_2$). In still other embodiments, the orthopedic implant workpiece 10 may be made from organic polymers or composites of organic polymers. Of course, persons of ordinary skill in the art may recognize that the processes disclosed herein may be used with other types of materials, and that the scope of the present disclosure should not be limited only to those materials mentioned above. The part platen 14 may be able to rotate about a center axis 18 and/or tilt about a vertical axis 20 to facilitate maximum exposure of the orthopedic implant workpiece 10 to an ion beam 22 during the silicon nitride implantation process. In one embodiment, the orthopedic implant workpiece 10 may couple to the part platen 14 via an attachment 24 that may include a grip, clamp, or other device having a high friction surface to retain (e.g., by compression fit) the orthopedic implant workpiece 10. In this respect, any attachment known in the art capable of sufficiently securing the orthopedic implant workpiece 10 to the part platen 14, as the part platen 14 rotates and/or tilts, will suffice. The vacuum chamber 16 maintains a high vacuum environment during the silicon nitride implantation process to promote the propagation of ions from the ion beam 22 toward the surfaces of the orthopedic implant workpiece 10. The high vacuum environment additionally reduces the amount of contaminant gases present to prevent contamination of a silicon nitride layer 26 (shown best in FIG. 5) subsequently bombarded or implanted into a surface 28 of the orthopedic implant workpiece 10. In further embodiments, a plurality of the part platens 12 may be present within the vacuum chamber 16 during the silicon nitride implantation process. In this embodiment, a plurality of the orthopedic implant workpieces 10 may be mounted in an array on each of the part platens 12 to produce multiple silicon nitride-implanted orthopedic implants 10 during each silicon nitride implantation process.

Once the orthopedic implant workpiece 10 has been mounted on the part platen 14, the next step (104), as shown in FIG. 1, is to energize an ion beam generator 30 to produce the ion beam 22 of energized nitrogen ions capable of penetrating into the surface 28 of the orthopedic implant workpiece 10 as it rotates about the center axis 18 and/or pivots about the vertical axis 20. Here, FIG. 2 illustrates the ion beam generator 30 emitting the ion beam 22 directed at the surface 28 of the orthopedic implant workpiece 10. In one example, the ion beam generator 30 can include a Kaufman ion source (e.g., a gridded broad beam ion source of permanent magnet design). The ion beam generator 30 can be capable of delivering nitrogen ions (e.g., N+ ions and/or N2+ ions) at beam energies up to 102 kiloelectron volts (KeV) at currents up to 6 mA. The ion beam 22 initially bombards the surface 28 of the orthopedic implant workpiece 10 with energized nitrogen ions during an ion beam cleaning process, thereby cleaning and augmenting the surface 28 of the orthopedic implant workpiece 10. Specifically, the initial bombardment of the orthopedic implant workpiece 10 during step (104) efficiently removes absorbed water vapor, hydrocarbons, and other substrate surface contaminants from the surface 28 of orthopedic implant workpiece 10. Removal of the substrate surface contaminants results in better implantation when the silicon nitride layer 26 is subsequently added to the subsurface of the orthopedic implant workpiece 10. Step (104) may also create defects in the surface 28 of orthopedic implant workpiece 10 which further promotes the subsequent implantation of the silicon nitride layer 26. At step (104) of the silicon nitride implantation process, relatively low energy ions (e.g., at beam energies between 1-1000 eV) can be employed to minimize sputtering at the surface 28 of orthopedic implant workpiece 10, while still being sufficiently energetic to produce the desired effects mentioned above.

Once the surface 28 of the orthopedic implant workpiece 10 has been cleaned and augmented by the ion beam 22, the next step (106) in accordance with FIG. 1 is to diffuse a gaseous mixture 32 of nitrogen gas ($N_2$) and vaporized silicon (Si) into the vacuum chamber 16. High purity nitrogen gas and a silicon ingot can be used as source materials to produce the gaseous mixture 32. In this regard, as shown in FIG. 2, an evaporator 34 located within the vacuum chamber 16 may produce a quantity of vaporized silicon atoms 36 by electron beam evaporation. Here, the evaporator 34 may direct an electron beam (not shown) at a silicon ingot workpiece (also not shown) to provide a direct flux of the vaporized silicon atoms 36, which disperse within vacuum chamber 16 as shown. The high purity nitrogen gas molecules 38 may then be subsequently introduced into the vacuum chamber 16 through an inlet 40. The nitrogen gas molecules 38 then mix with the vaporized silicon atoms 36 to form the gaseous mixture 32. The ion beam 22 may then energize the resulting gaseous mixture 32 to form silicon nitride molecules 42, as discussed in detail herein.

Once the gaseous mixture 32 has been introduced into the vacuum chamber 16, the next step (108) as shown in FIG. 1 is to promote and control the reaction of the vaporized silicon atoms 36 and the nitrogen gas molecules 38 in gaseous mixture 32 using the ion beam 22, as shown in FIGS. 3a-3b. First, the positively charged nitrogen ions of the ion beam 22 collide with and kinetically excite the vaporized silicon atoms 36 and the nitrogen gas molecules 38 to promote the reaction process generally shown in FIG. 3a. Once kinetically excited, the vaporized silicon atoms 36 react with the nitrogen gas molecules 38 to form the gaseous silicon nitride molecules 42 as shown in FIG. 3b. The rate of formation of the gaseous silicon nitride molecules 42 can be controlled by varying the energy and/or the density of the ion beam 22. For example, increasing the energy and/or density of the ion beam 22 increases the rate of formation of the gaseous silicon nitride molecules 42, and vice versa. As the vaporized silicon atoms 36 and the nitrogen gas molecules 38 react during step (108) to form gaseous silicon nitride molecules 42, a controlled backfill of vaporized silicon atoms 36 and/or the nitrogen gas molecules 38 may be employed to maintain the desired concentration of reactant molecules in the vacuum chamber 16.

In some embodiments of the processes disclosed herein, steps (106) and (108) may be performed without halting the cleaning process described in step (104). That is, the vaporized silicon atoms 36 and the nitrogen gas molecules 38 may be introduced into the vacuum chamber 16 without halting the ion beam cleaning process of step (104). In this way, the ion beam 22 immediately begins promoting the reaction of the vaporized silicon atoms 36 and the nitrogen gas molecules 38 once introduced into vacuum chamber 16. This can be more efficient from a manufacturing standpoint by reducing the duration required to perform the silicon nitride implantation process disclosed herein. Additionally, introducing the vaporized silicon atoms 36 and the nitrogen gas molecules 38 without halting the cleaning process can prevent subsequent contamination of the substrate surface 28. This may further promote generation of the subsurface silicon nitride layer 26 in the surface 28 of the orthopedic implant workpiece 10.

Once the gaseous silicon nitride molecules 42 are formed, the ion beam 22 subsequently drives the silicon nitride molecules 42 into the surface 28 of the rotating and/or pivoting orthopedic implant workpiece 10, per step (110) in FIG. 1. The high-energy nitrogen ions of the ion beam 22 collide with the silicon nitride molecules 42 to impart kinetic energy thereto. The energized silicon nitride molecules 42 subsequently collide with the surface 28 of the orthopedic implant workpiece 10 and bombard or implant therein, thereby initially forming a subsurface intermixed layer 44, as shown in FIG. 4a. The silicon nitride molecules 42 bombarded or implanted therein integrate with the surface 28, as opposed to simply be deposited on the surface 28 as an over surface coating, as is the current practice with known silicon nitride deposition procedures. The intermixed layer 44 is basically a transition region wherein the surface molecules 46 of the orthopedic implant workpiece 10 become intermixed with the silicon nitride molecules 42 as a result of the energized bombardment by way of the ion beam 22. The accumulation of silicon nitride molecules 42 within the intermixed layer 44 results in alloyed silicon nitride molecules 42 and substrate molecules 46. By varying the energy and/or density of the beam 22, persons skilled in the art can vary the depth into which the silicon nitride molecules 42 are driven.

As the intermixed layer 44 develops, the ion beam 22 continues to drive the silicon nitride molecules 42 into the subsurface of the surface 28 of the orthopedic implant workpiece 10. As shown in FIG. 4b, through time, the silicon nitride layer 26 subsequently begins to form above the intermixed layer 44. The depth the silicon nitride layer 26 forms into the subsurface of the surface 28 varies according to various variables, including the energy and/or density of the ion beam 22 (i.e., higher energy or a greater density results in a thicker or deeper silicon nitride layer 26, and vice versa) and/or the duration of bombardment with the ion beam 22 (i.e., a longer bombardment in a particular area may result in a thicker or deeper silicon nitride layer 26, and vice versa). Similarly, varying the rate of nitrogen ion arrival can affect the stoichiometry of the resulting silicon nitride layer 26. For example, the nitrogen ion arrival rate may be in the range of about one (1) nitrogen ion to about five (5) nitrogen ions for each silicon atom in the gaseous mixture 32. In some embodiments of the processes disclosed herein, a nitrogen ion arrival rate closer to one (1) ion for each silicon atom can result in the silicon nitride layer 26 that includes $Si_3N_4$. In other embodiments, a nitrogen ion arrival rate closer to five (5) ions for each silicon atom can result in a silicon nitride layer 26 that includes $SiN_3$. Persons of ordinary skill in the art may vary the nitrogen ion arrival rate to obtain a silicon nitride phase suitable for the desired application.

As a result of step (110), the silicon nitride layer 26 is molecularly integrated into the subsurface of the surface 28 (e.g., as shown in FIG. 5) of the orthopedic implant workpiece 10 and exhibits superior retention relative to silicon nitride coatings simply deposited as an over coating on the surface 28 by traditional PVD processes. This is due, at least in part, to the high strength of the alloy bond formed at an atomic level by the ion bombardment, which creates the intermixed layer 44 between the silicon nitride layer 26 and the surface molecules 46 of the orthopedic implant workpiece 10. As such, this ultimately changes the atomic foundation of the subsurface of the orthopedic implant workpiece 12. As the bombardment continues, the outermost silicon nitride layer 26 builds up, and does so over the entire orthopedic implant workpiece 12 as it rotates and/or pivots with the part platen 14. Although, of course, the processes disclosed herein may include application to only a part of the orthopedic implant workpiece 12, e.g., the articulation surfaces, as opposed to the entire orthopedic implant workpiece 12. The articulation surfaces may later be polished, along with adjacent surfaces or other fixation surfaces. The material properties of the orthopedic implant workpiece 12, in combination with the energy intensity characteristics of the ion beam 22, limit the penetration depth to attain a more consistently uniform silicon nitride layer 26. In this regard, the silicon nitride layer 26 is less likely to delaminate from the orthopedic implant workpiece 10 when compared to conventional PVD coatings. As such, the processes and implants disclosed herein are able to attain the benefits of silicon nitride across different types of surface finishes and surface requirements of an orthopedic implant.

During step (110), the surface 28 of the orthopedic implant workpiece 10 increases in temperature as a result of bombardment by the ion beam 22. As such, a cooler can be utilized to cool the silicon nitride layer 26, the intermixed layer 44, and/or orthopedic implant workpiece 10 in general to prevent adverse or unexpected changes in the material properties due to heating. In this respect, cooling may occur in and/or around the area of the orthopedic implant workpiece 10 being bombarded or implanted with the silicon nitride layer 26, and including the part platen 14. Water or air circulation-based coolers may be used with the processes disclosed herein to provide direct or indirect cooling of the orthopedic implant workpiece 10.

FIG. 5 is a diagrammatic cross-sectional view illustrating the surface 28 of the orthopedic implant workpiece 10, including the resultant intermixed layer 44 and the silicon nitride layer 26 formed into the subsurface thereof. The processes disclosed herein result in the intermixed layer 44 having a thickness 48 and the silicon nitride layer 26 having an implantation thickness 50, as shown in FIG. 5. The intermixed layer 44 is positioned generally between the unaffected surface molecules 46 and the silicon nitride layer 26. Accordingly, the intermixed layer 44 may form a uniform layer immediately above the unaffected surface molecules 46, such as designated by a boundary 52, and the silicon nitride layer 26 may form a uniform layer immediately above the intermixed layer 44, such as designated by a boundary 54. The intermixed width 48 and the depth of the boundary 52 may vary depending on the energy and/or density of the ion beam 22, to increase (i.e., higher energy and/or density) or decrease (i.e., lower energy and/or density) the integration or implantation of the silicon nitride molecules 42 into the subsurface of the surface 28 of the orthopedic implant workpiece 10. Likewise, the implantation thickness 50 and the depth of the boundary 54 may vary depending on the energy and/or density of the ion beam 22, to increase (i.e., higher energy and/or density) or decrease (i.e., lower energy and/or density) the integration or implantation of the silicon nitride molecules 42 into the subsurface of the surface 28 of the orthopedic implant workpiece 10. In an exemplary embodiment, the intermixed width 48 may be between 0.1-100 nanometers, while the implantation thickness 50 may be between 1-10,000 nanometers.

The resulting silicon nitride layer 26 may exhibit excellent tribological properties, including long-term material stability and high biocompatibility, at least relative to alumina. Likewise, silicon nitride is semitransparent to X-rays and is not magnetic, thereby allowing MRI of soft tissues proximal to silicon nitride coated implants. Meanwhile, silicon nitride also has wear rates comparable to alumina. Furthermore, unlike zirconia, which is a good conductor of electricity, silicon nitride advantageously has high electrical resistivity, such as on the order of $10^{16}$ Ω·cm.

Although several embodiments have been described in detail for purposes of illustration, various modifications may be made without departing from the scope and spirit of the invention. Accordingly, the invention is not to be limited, except as by the appended claims.

What is claimed is:

1. A process for producing an orthopedic implant having an integrated silicon nitride surface layer, comprising the steps of:
    positioning the orthopedic implant inside a vacuum chamber;
    vaporizing silicon atoms inside the vacuum chamber;
    mixing nitrogen gas and the vaporized silicon atoms in the vacuum chamber;
    emitting a relatively high energy beam comprising an energy level greater than 102 kiloelectron volts (KeV) into the mixture of nitrogen gas and vaporized silicon atoms in the vacuum chamber to cause a gas-phase reaction between the nitrogen gas and the vaporized silicon atoms to form reacted precipitate silicon nitride molecules;
    driving the precipitate silicon nitride molecules with the same beam into an outer surface of the orthopedic implant at a relatively high energy such that the precipitate silicon nitride molecules implant therein and form at least a part of the molecular structure of the outer surface of the orthopedic implant simultaneously while maintaining the outer surface of the orthopedic implant at a temperature below 200 degrees Celsius, thereby forming the integrated silicon nitride surface layer; and
    forming an intermix layer underneath the integrated silicon nitride surface layer, the intermix layer including a mixture of subsurface level precipitate silicon nitride molecules and a base material of the orthopedic implant,
    wherein the intermix layer is molecularly integrated with the base material,
    wherein the integrated silicon nitride surface layer and the base material cooperate to sandwich the intermix layer in between.

2. The process of claim 1, wherein the beam comprises an ion beam comprising nitrogen ions selected from the group consisting of N+ ions or N2+ ions.

3. The process of claim 2, wherein the emitting step includes the step of delivering the nitrogen ions at a rate of about 1-5 nitrogen ions for each vaporized silicon atom.

4. The process of claim 3, wherein, when the rate is about one nitrogen ion for each silicon atom, the integrated silicon nitride surface layer includes Si3N4, and, when the rate is about five nitrogen ions for each silicon atom, the integrated silicon nitride surface layer includes SiN3.

5. The process of claim 1, including the step of cleaning the outer surface of the orthopedic implant with the beam at an energy level between about 1-1000 electron volts.

6. The process of claim 1, wherein the positioning step includes the step of mounting the orthopedic implant to a selectively movable platen for repositioning an orientation of the orthopedic implant relative to the beam.

7. The process of claim 1, including the step of vaporizing silicon atoms off a silicon ingot with an evaporator.

8. The process of claim 1, including the step of propagating the beam.

9. The process of claim 1, including the step of regulating a formation rate of the precipitate silicon nitride molecules by adjusting the beam energy or beam density.

10. The process of claim 1, including the step of backfilling the vacuum chamber with the nitrogen gas or the vaporized silicon atoms.

11. The process of claim 1, wherein the integrated silicon nitride surface layer substantially comprises the silicon nitride molecules.

12. The process of claim 1, wherein the driving step includes the step of applying the integrated silicon nitride surface layer to less than an entire outer surface area of the orthopedic implant.

13. The process of claim 1, wherein the integrated silicon nitride surface layer comprises a substantially uniform thickness where driven into the orthopedic implant.

14. A process for producing an orthopedic implant having an integrated silicon nitride surface layer, comprising the steps of:
    positioning the orthopedic implant inside a vacuum chamber;
    vaporizing silicon atoms off a silicon ingot with an evaporator;
    mixing nitrogen gas and the vaporized silicon atoms in the vacuum chamber;
    emitting a relatively high energy beam comprising an energy level greater than 102 kiloelectron volts (KeV) into the mixture of nitrogen gas and vaporized silicon atoms in the vacuum chamber to cause a gas-phase reaction between the nitrogen gas and the vaporized silicon atoms to form reacted precipitate silicon nitride molecules;
    cleaning an outer surface of the orthopedic implant with the beam at an energy level between about 1-1000 electron volts;
    driving the precipitate silicon nitride molecules with the same beam into the outer surface of the orthopedic implant at a relatively high energy such that the precipitate silicon nitride molecules implant therein and form at least a part of the molecular structure of the outer surface of the orthopedic implant simultaneously while maintaining the outer surface of the orthopedic implant at a temperature below 200 degrees Celsius, thereby forming the integrated silicon nitride surface layer; and
    forming an intermix layer underneath the integrated silicon nitride surface layer, the intermix layer including a mixture of subsurface level precipitate silicon nitride molecules and a base material of the orthopedic implant,
    wherein the intermix layer is molecularly integrated with the base material,
    wherein the integrated silicon nitride surface layer and the base material cooperate to sandwich the intermix layer in between.

15. The process of claim 14, wherein the beam comprises an ion beam comprising nitrogen ions selected from the group consisting of N+ ions or N2+ ions and the emitting step includes the step of delivering the nitrogen ions at a rate of about 1-5 nitrogen ions for each vaporized silicon atom.

16. The process of claim 15, wherein, when the rate is about one nitrogen ion for each silicon atom, the integrated silicon nitride surface layer includes Si3N4, and, when the rate is about five nitrogen ions for each silicon atom, the integrated silicon nitride surface layer includes SiN3.

17. The process of claim 14, wherein the positioning step includes the step of mounting the orthopedic implant to a selectively movable platen for repositioning an orientation of the orthopedic implant relative to the beam.

18. The process of claim 14, including the step of propagating the beam, wherein the integrated silicon nitride surface layer substantially comprises the silicon nitride molecules.

19. The process of claim 14, including the step of regulating a formation rate of the precipitate silicon nitride molecules by adjusting the beam energy or beam density, wherein the driving step includes the step of applying the integrated silicon nitride surface layer to less than an entire outer surface area of the orthopedic implant.

20. The process of claim 14, including the steps of backfilling the vacuum chamber with the nitrogen gas or the vaporized silicon atoms, wherein the integrated silicon nitride surface layer comprises a substantially uniform thickness where driven into the orthopedic implant.

\* \* \* \* \*